United States Patent [19]

Robertson et al.

[11] Patent Number: 5,135,947
[45] Date of Patent: Aug. 4, 1992

[54] 1-PHENYL-3-NAPHTHALENYLOXY-PROPANAMINES AND THEIR USE AS SELECTIVE SEROTONIN REUPTAKE INHIBITORS

[75] Inventors: David W. Robertson, Greenwood; David T. Wong; Dennis C. Thompson, both of Indianapolis, all of Ind.

[73] Assignee: Eli Lilly and Company, Indianapolis, Ind.

[21] Appl. No.: 561,492

[22] Filed: Aug. 1, 1990

Related U.S. Application Data

[63] Continuation of Ser. No. 372,149, Jun. 26, 1989, abandoned, which is a continuation of Ser. No. 191,465, May 9, 1988, abandoned, which is a continuation-in-part of Ser. No. 36,534, Apr. 9, 1987, abandoned.

[51] Int. Cl.$^5$ .................. A61K 31/36; A61K 31/205; C07D 317/58; C07C 217/20
[52] U.S. Cl. .................................... 514/466; 514/554; 514/651; 549/443; 562/585; 564/352
[58] Field of Search ................ 564/352; 514/651, 555, 514/554, 466; 549/443; 562/585

[56] References Cited

U.S. PATENT DOCUMENTS

| 4,018,895 | 4/1977 | Molloy et al. | 424/330 |
| 4,194,009 | 3/1980 | Molloy et al. | 424/330 |
| 4,207,343 | 5/1980 | Lavagnino et al. | 424/330 |
| 4,314,081 | 2/1982 | Molloy et al. | 564/347 |
| 4,329,356 | 5/1982 | Holland | 424/274 |

FOREIGN PATENT DOCUMENTS 2060618  5/1981  United Kingdom.

OTHER PUBLICATIONS

Cronenberger et al., Chemie Therapeutique, 5/6, 289 (1966).

Primary Examiner—Nicky Chan
Attorney, Agent, or Firm—Robert A. Conrad; Leroy Whitaker

[57] ABSTRACT

The present invention provides 1-phenyl-3-naphthalenyloxypropanamines which are selective inhibitors of serotonin uptake.

53 Claims, No Drawings

1-PHENYL-3-NAPHTHALENYLOXYPROPANA-MINES AND THEIR USE AS SELECTIVE SEROTONIN REUPTAKE INHIBITORS

This application is a continuation of application Ser. No. 07/372,149, filed on Jun. 26, 1989, now abandoned, which is a continuation of application Ser. No. 07/191,465, filed on May 9, 1988, now abandoned, which is a continuation-in-part of copending application U.S. Ser. No. 07/036,534, filed on Apr. 9, 1987, now abandoned.

BACKGROUND OF THE INVENTION

During the past decade, the relationship between monoamine uptake and a variety of diseases and conditions has been appreciated and investigated. For example, the hydrochloride salt of fluoxetine (dl-N-methyl-3-phenyl-3-[4-(trifluoromethyl)phenoxy]propanamine) is a selective serotonin (5-hydroxytryptamine) uptake inhibitor presently undergoing clinical evaluation for the treatment of depression, eating disorders, alcoholism, and other disorders. Similarly, tomoxetine hydrochloride ((−)-N-methyl-3-phenyl-3-(2-methylphenoxy)propanamine hydrochloride) is a selective inhibitor of norepinephrine uptake being investigated clinically for its antidepressant activity. These compounds are among many taught in U.S. Pat. Nos. 4,018,895, 4,194,009, and 4,314,081 as being potent blockers of the uptake of various physiologically active monoamines including serotonin, norepinephrine and dopamine.

U.S. Pat. No. 4,207,343 discloses 1-phenyl-3-(substituted phenoxy)propanamines again having the ability to block the uptake of a variety of monoamines.

SUMMARY OF THE INVENTION

The present invention provides novel 1-phenyl-3-naphthalenyloxypropanamines which are selective inhibitors of serotonin uptake and which do not have a direct effect on neuronal receptors, and would therefore be expected to produce fewer side effects following administration since the compounds do not effectively block other monoamines. More specifically, the present invention relates to a compound of the formula

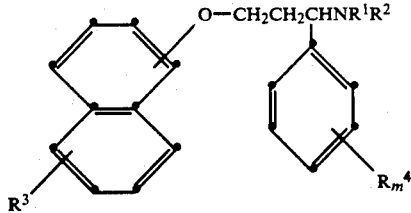

wherein:
each of $R^1$ and $R^2$ independently is hydrogen or methyl;
$R^3$ is hydrogen, halo, $C_1$-$C_4$ alkyl, $C_1$-$C_3$ alkoxy or trifluoromethyl;
each $R^4$ independently is hydrogen, halo, $C_1$-$C_4$ alkyl, $C_1$-$C_3$ alkoxy or trifluoromethyl;
m is 1 or 2;
when m is 2, each $R^4$ can be combined to form methylenedioxy; and
the pharmaceutically acceptable acid addition salts thereof.

The invention also provides pharmaceutical formulations comprising a compound of the above formula and a pharmaceutically acceptable carrier, diluent or excipient therefor.

A further embodiment of the invention are methods for selectively inhibiting the uptake of serotonin, as well as for treating a variety of disorders which have been linked to decreased neurotransmission of serotonin in mammals including obesity, depression, alcoholism, pain, loss of memory, anxiety, smoking, and the like, employing a compound of the invention.

DETAILED DESCRIPTION OF THE INVENTION

In the above formula, the term $C_1$-$C_4$ alkyl represents a straight or branched alkyl chain bearing from one to four carbon atoms. Typical $C_1$-$C_4$ alkyl groups include methyl, ethyl, n-propyl, isopropyl, n-butyl, isobutyl, sec.-butyl and t-butyl.

$C_1$-$C_3$ Alkoxy represents methoxy, ethoxy, n-propoxy or isopropoxy.

Halo represents fluoro, chloro, bromo or iodo.

The naphthalenyl substituent can be either 1-naphthalenyl or 2-naphthalenyl.

While all of the compounds of the present invention are believed to inhibit the uptake of serotonin in mammals, there are certain of these compounds which are preferred for such uses. Preferably one of $R^1$ and $R^2$ is hydrogen and the other is methyl. Especially preferred is where both $R^1$ and $R^2$ are methyl. Other preferred aspects of the present invention will be noted hereinafter.

The compounds of the present invention possess an asymmetric carbon represented by the carbon atom labeled "C" in the following formula:

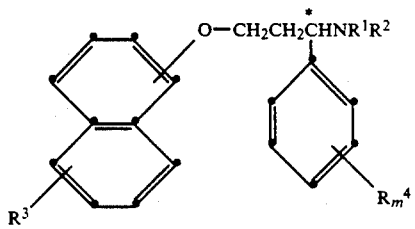

As such, the compounds can exist as the individual stereoisomers, as well as the racemic mixture of such isomers. Accordingly, the compounds of the present invention will include not only the dl-racemates, but also their respective optically active d- and l-isomers.

As pointed out above, the invention includes the pharmaceutically acceptable acid addition salts of the compounds defined by the above formula. Since the compounds of this invention are amines, they are basic in nature and accordingly react with any number of inorganic and organic acids to form pharmaceutically acceptable acid addition salts. Since the free amines of the invention are typically oils at room temperature, it is preferable to convert the free amines to their corresponding pharmaceutically acceptable acid addition salts, which are routinely solid at room temperature, for ease of handling. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, $\beta$-hydroxybutyrate, glycollate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such oxalic acid and maleic acid.

The following compounds further illustrate compounds contemplated within the scope of the present invention:

N-Methyl-1-phenyl-3-(1-naphthalenyloxy)propanamine phosphate

N-Methyl-1-(4-methylphenyl)-3-(2-naphthalenyloxy)propanamine citrate

N,N-Dimethyl-1-(3-bromophenyl)-3-(4-chloro-1-naphthalenyloxy)propanamine hydrochloride N-Methyl-1-(3-chlorophenyl)-3-(5-methyl-2-naphthalenyloxy)propanamine hydrobromide N-Methyl-1-(2-ethylphenyl)-3-[3-(trifluoromethyl)-1-naphthalenyloxy]propanamine oxalate N-Methyl-1-(4-fluorophenyl)-3-(6-iodo-1-naphthalenyloxy)propanamine maleate N,N-Dimethyl-1-(3-methoxyphenyl)-3-(1-naphthalenyloxy)propanamine formate N,N-Dimethyl-1-(4-n-propylphenyl)-3-(2-naphthalenyloxy)propanamine N-Methyl-1-[3-(trifluoromethyl)phenyl]-3-(1-naphthalenyloxy)propanamine sulfate N-Methyl-1-(4-methylphenyl)-3-(4-methyl-1-naphthalenyloxy)propanamine oxalate N-Methyl-1-(2-bromophenyl)-3-(2-naphthalenyloxy)propanamine hydrochloride N,N-Dimethyl-1-(4-ethoxy-3-chlorophenyl)-3-(6-iodo-2-naphthalenyloxy)propanamine malonate N,N-Dimethyl-1-(2-ethylphenyl)-3-(1-naphthalenyloxy)propanamine hydroiodide N,N-Dimethyl-1-(3,4-difluorophenyl)-3-(4-methyl-2-naphthalenyloxy)propanamine maleate N-Methyl-1-(4-chlorophenyl)-3-(2-naphthalenyloxy)propanamine caprate N-Methyl-1-(2-methoxyphenyl)-3-(6-n-propyl-1-naphthalenyloxy)propanamine citrate N,N-Dimethyl-1-(3-ethylphenyl)-3-(2-methyl-1-naphthalenyloxy)propanamine monohydrogen phosphate 1-(4-Bromophenyl)-3-(1-naphthalenyloxy)propanamine succinate 1-(3,4-Dimethylphenyl)-3-[3-(trifluoromethyl)-1-naphthalenyloxy]propanamine acetate N-Methyl-1-(4-methoxyphenyl)-3-(6-methyl-1-naphthalenyloxy)propanamine tartrate 1-(2-Iodophenyl)-3-(2-naphthalenyloxy)propanamine N-Methyl-1-(3-methylphenyl)-3-(4-n-butyl-1-naphthalenyloxy)propanamine methanesulfonate 1-(4-Chlorophenyl)-3-(2-chloro-1-naphthalenyloxy)propanamine oxalate N-Methyl-1-phenyl-3-(1-naphthalenyloxy)propanamine tartrate The compounds of the present invention may be prepared by procedures well known to those of ordinary skill in the art. The compounds are preferably synthesized by reacting a 2-naphthalenyloxyethylhalide derivative with a phenylacetic acid dianion to provide the corresponding 1-carboxy-1-phenyl-3-naphthalenyloxypropane. This compound is converted to the corresponding 1-isocyano-1-phenyl-3-naphthalenyloxypropane which is reduced to the corresponding 1-phenyl-3-naphthalenyloxypropanamine of the invention. This compound may then be converted to the N-methyl or N,N-dimethyl analog, if desired. The scheme for this reaction is represented by the following:

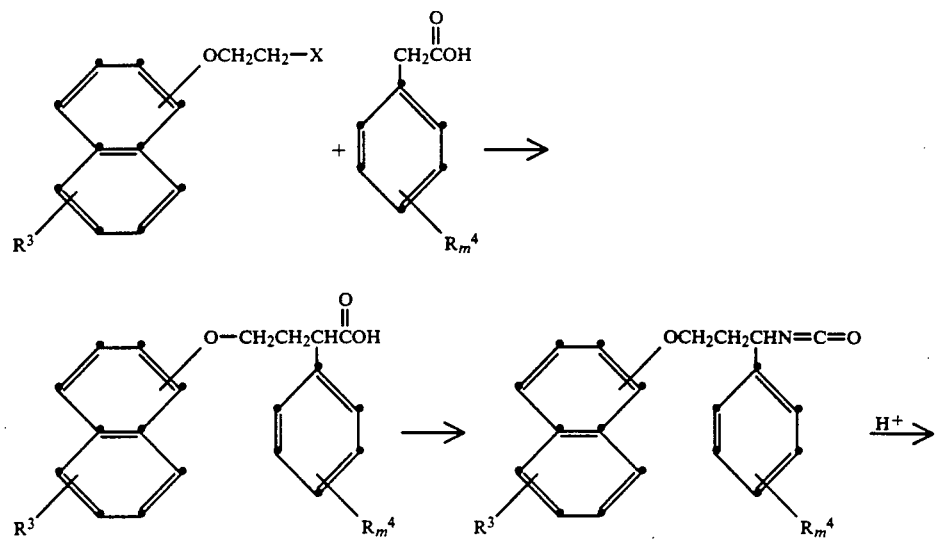

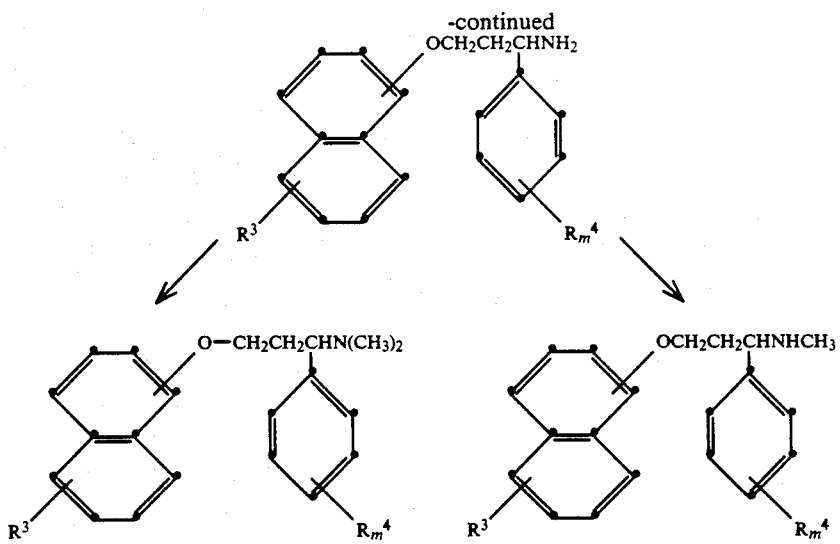

wherein $R^3$, $R^4$ and m are as defined above and X is halogen.

According to the first step of the reaction, a phenylacetic acid derivative is dissolved in a mutual solvent under anhydrous conditions. To this mixture is added an alkyl alkali metal reagent and a suitable condensing agent. Typical solvents suitable for use in this reaction are preferably dried and include the aprotic solvents such as the ethers, for example diethyl ether, and the cyclic ethers, such as tetrahydrofuran, which is preferred. Exemplary alkyl alkali metal reagents include sec.-butyl lithium and n-butyl lithium, which is preferred. A typical and preferred condensing agent is hexamethylphosphoramide (HMPA). The reaction is typically cooled to a temperature in the range of about −100° C. to about −25° C., more preferably at a temperature in the range of about −80° C. to about −70° C., and a dilute solution of an equimolar quantity of the 2-naphthalenyloxyethyl halide is added dropwise to the mixture. The mixture is allowed to stir for approximately 8 to 24 hours and is diluted with water. The desired product is isolated by acidifying the mixture with a suitable acid and extracting the mixture with a suitable water immiscible organic solvent such as diethyl ether. The solvent is removed, preferably by evaporation under vacuum, and the resulting product is further purified, if desired, by standard techniques such as purification over solid supports, such as silica gel or alumina, or crystallization from common solvents.

In the second step of the above described process, the 1-carboxy-1-phenyl-3-naphthalenyloxypropane thus synthesized is converted to the corresponding 1-isocyanato-1-phenyl-3-naphthalenyloxypropane. This reaction was conducted by dissolving the carboxylic acid derivative in a suitable solvent and cooling the resulting mixture to about 0° C. To this mixture a suitable base such as triethylamine is added followed by the dropwise addition of chloroethylformate. To this mixture is added dropwise approximately equimolar quantities of sodium azide dissolved in a small amount of water. The reaction is substantially completed after about 30 minutes to about 12 hours when conducted at a temperature in the range of about 0° C. to about 20° C. The reaction mixture is extracted with a suitable water immiscible solvent and the resulting organic solution containing the product is purified according to standard procedures. The resulting acylazide intermediate is combined with an inert solvent, such as toluene, and stirred at a temperature in the range of about 25° C. to about 110° C. to provide the desired isocyanato compound.

The compound of the invention wherein $R^1$ and $R^2$ are both hydrogen is finally synthesized by hydrolyzing the 1-isocyanato compound of the invention with a suitable acid. Typical acids include the hydrohalic acids such as hydrochloric acid. The reaction is substantially complete after about 1 hour to about 24 hours when conducted at a temperature in the range of about 20° C. to about 100° C. The desired product is isolated by raising the pH of the reaction mixture to approximately 8, and either isolating the desired compound by extraction by a suitable water immisible solvent or collecting the precipitated product by vacuum filtration. The product thus synthesized can be further purified if desired by standard procedures.

Compounds of the present invention wherein $R^1$ and $R^2$ are both methyl are synthesized by reacting the primary amine compound of the invention with an excess of formaldehyde in the presence of sodium cyanoborohydride and a mutual solvent.

Compounds of the present invention wherein one of $R^1$ and $R^2$ is methyl and the other is hydrogen are prepared by reacting the primary propanamine with ethylchloroformate in the presence of triethylamine and a suitable solvent to provide the corresponding carbamate intermediate, which is then reduced in the presence of a suitable reducing agent such as lithium aluminum hydride to provide the N-methyl compounds of the present invention.

Certain of the compounds of the invention may also be synthesized by reacting a benzaldehyde derivative with malonic acid and ammonium acetate to provide the corresponding 1-phenyl-2-carboxyethanamine. This compound may be either dimethylated on the amine nitrogen atom or left as the primary amine. Either of these compounds is then converted to the corresponding carboxylic acid ester, which is reduced to the alcohol. The compounds of the invention are synthesized by treating the resulting hydroxy intermediate with an alkali metal hydride to form the corresponding alkali metal salt, which is then reacted with an appropriate compound containing a good leaving group to provide the corresponding 1-phenyl-3-naphthalenyloxypropanamine of the invention. This reaction may be represented by the following scheme:

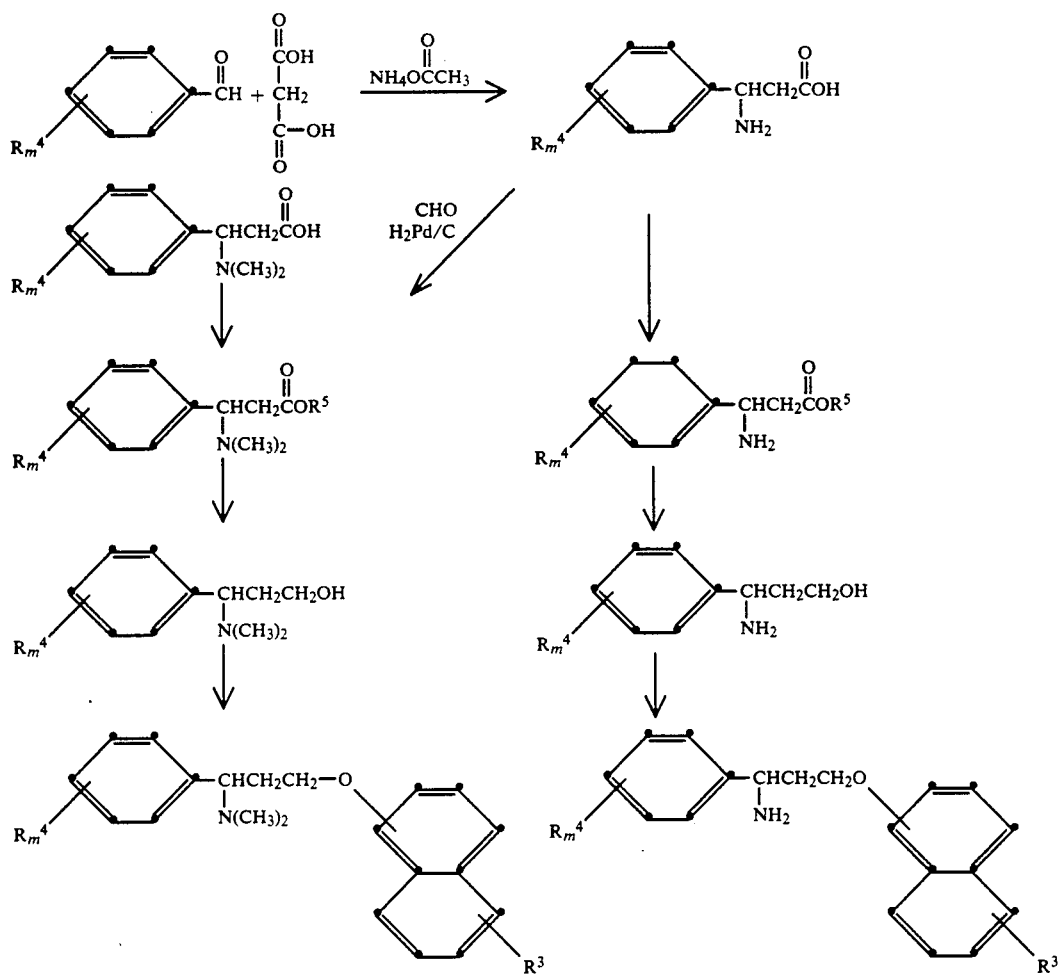

wherein $R^1$, $R^2$, $R^3$, $R^4$ and m are as defined above, and $R^5$ is $C_1$-$C_4$ alkyl.

The final step of the foregoing reaction sequence is carried out by combining approximately equimolar quantities to a slight excess of the alkali metal hydride with the alcohol to provide the corresponding alkali metal salt. Typical alkali metal hydrides include sodium hydride and potassium hydride. The compound is then reacted with an equimolar quantity to slight excess of the compound having the good leaving group. The reaction is conducted in a suitable aprotic solvent such as N,N-dimethylacetamide and related solvents. The reaction is substantially complete after about 10 minutes to about 24 hours when conducted at a temperature in the range of about 25° C. to about 150° C. More preferably, the reaction mixture will be complete within about 30 minutes to about 6 hours when conducted at a temperature in the range of about 75° C. to about 125° C. The product may be isolated by standard conditions as well. Typically, the mixture is diluted with water and extracted with a water immiscible organic solvent such as diethyl ether, ethyl acetate, chloroform and the like. The organic extracts are typically combined and dried. Following evaporation of the organic solvent the isolated residue may be further purified, if desired, by standard techniques such as crystallization from common solvents, or chromatography over solid supports such as silica gel or alumina.

The compounds of the invention may also be prepared by reacting a hydroxy substituted naphthalene with a 3-phenylpropyl halide to provide the corresponding 1-phenyl-3-naphthalenyloxypropane, which is brominated and aminated to provide a compound of the invention. This reaction may be represented by the following scheme:

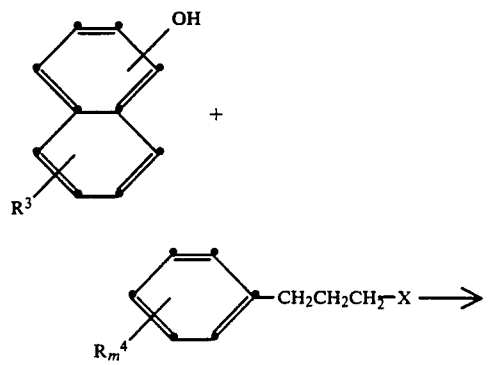

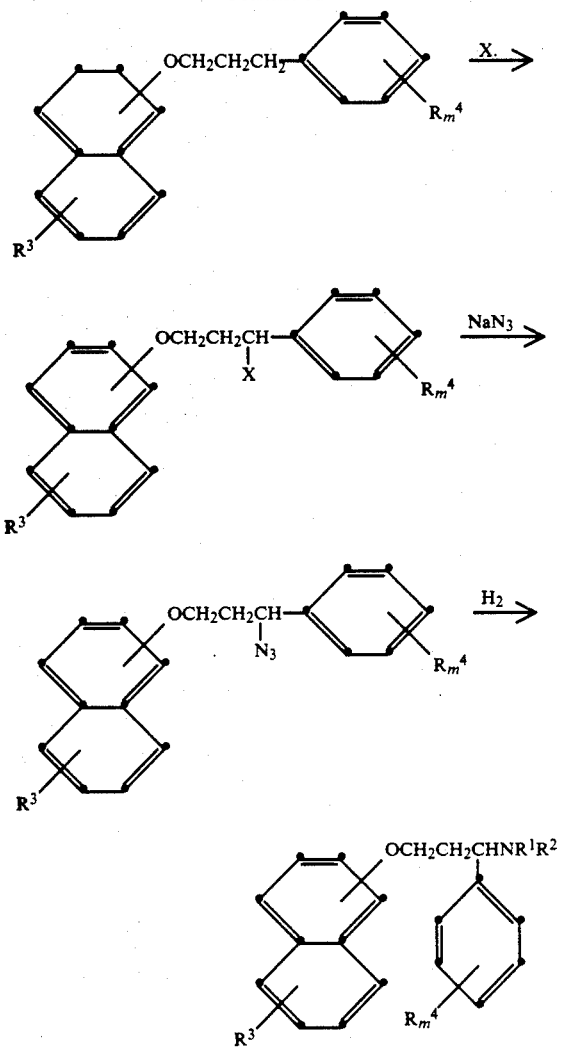

wherein $R^1$, $R^2$, $R^3$, $R^4$ and m are as defined above and X is halogen.

The first step of the above described process is carried out by adding the hydroxy substituted naphthalene to a solution of a suitable base dissolved in a mutual solvent. Suitable bases include the alkali metal hydroxides such as sodium hydroxide and especially potassium hydroxide. Typical solvents suitable for this reaction include the alcohols such as methanol. Following complete reaction of the base and the hydroxy naphthalene compound, which generally takes from a few minutes to four hours, the 3-phenylpropylhalide is added to the reaction mixture. The reaction is substantially complete after about 1 to 24 hours when conducted at a temperature in the range of about 25° C. to about 150° C., more preferably in about 8 hours when conducted at the reflux temperature of the reaction mixture. The product is then isolated by standard procedures and purified, if desired.

In the second step of the reaction, the carbon atom adjacent to the phenyl ring is halogenated. This reaction is conducted with any of a variety of halogenating agents preferably N-bromosuccinimide.

The resulting halogenated intermediate is next reacted with sodium azide, and then hydrogenated to provide the compounds of the invention wherein $R^1$ and $R^2$ are both hydrogen. Alternatively, the halogenated intermediate can be treated with an appropriate aminating agent $NHR^1R^2$ to provide a compound of the invention.

The compounds of the present invention wherein one of $R^1$ and $R^2$ is hydrogen and the other is methyl may also be prepared by demethylating the corresponding N,N-dimethylpropanamine. Preferably, a reagent such a phenyl chloroformate or trichloroethyl chloroformate is reacted with the N,N-dimethylpropanamine to provide the corresponding intermediate, which is then hydrolyzed to provide the corresponding N-methylpropanamine.

As noted above, the optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents include dibenzoyl-d- and -l-tartaric acids and especially d- and 1-3-bromocamphor-8-sulfonic acid (ammonium salt) and the like.

The compounds employed as starting materials in the synthesis of the compounds of the invention are well known and readily synthesized by standard procedures commonly employed by those of ordinary skill in the art.

The pharmaceutically acceptable acid addition salts of the invention are typically formed by reacting a 1-phenyl-3-naphthalenyloxypropanamine of the invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

EXAMPLE 1

1-Phenyl-3-(4-methyl-1-naphthalenyloxy)propanamine oxalate

A. 2-(4-Methyl-1-naphthalenyloxy)ethylchloride.

A 250 ml three-neck round bottom flask fitted with a thermometer, nitrogen inlet tube and magnetic stirrer was charged with 1.09 g (6.9 mmol) of 4-methyl-1-naphthol and 75 ml of N,N-dimethylformamide. To the mixture was added 331 mg (8.3 mmol) of sodium hydride and the resulting mixture was stirred for approximately 15 minutes. Next, 1.6 ml (13.8 mmol) of 2-chloroethylmethanesulfonate was added and the resulting mixture was heated at about 70° C. for approximately 16 hours. The mixture was cooled and diluted with water. The mixture was extracted twice with diethyl ether. The organic extracts were combined and washed twice with water, once with a saturated sodium chloride solution and dried over anhydrous sodium sulfate. The mixture was filtered and concentrated under vacuum to provide 1.8 g of a dark oil. This material was combined with approximately 19 g of additional material prepared by the same process and purified by high pressure liquid chromatography to provide 9.76 g. A NMR of the material verified the structure of the desired compound.

B. 1-Carboxy-1-phenyl-3-(4-methyl-1-naphthalenyloxy)propane

To a 1 l. three-neck round bottom flask fitted with a thermometer, nitrogen inlet tube, addition funnel and magnetic stirrer was added 5.9 g (43.6 mmol) of phenylacetic acid and 250 ml of tetrahydrofuran. To the mixture was added 7.6 ml (43.6 mmol) of HMPA. The mixture was cooled to approximately 0° C. and 6.4 ml (89.4 mmol) of 1.48M n-butyllithium was added dropwise to the reaction mixture. The mixture was warmed to room temperature over a period of approximately 50 minutes and cooled to approximately −78° C. To the reaction mixture was added a solution of 2-(4-methyl-1-naphthalenyloxy)ethyl chloride dissolved in 100 ml of THF. The reaction mixture was stirred at room temperature overnight and diluted with water. The mixture was washed twice with diethyl ether and the resulting aqueous phase was acidified. The aqueous phase was extracted twice with diethyl ether and the organic extracts were combined, washed twice with water, once with a saturated sodium chloride solution and dried over anhydrous sodium sulfate. The volatile constituents were evaporated under vacuum to provide 9.53 g of a light tan solid. The solid was recrystallized from diethyl ether and hexane to provide 5.62 g of the desired product. mp=130°–131.5° C.

Analysis calculated for $C_{21}H_{20}O_3$: Theory: C, 78.73; H, 6.29; Found: C, 78.95; H, 6.22.

C. 1-Isocyanato-1-phenyl-3-(4-methyl-1-naphthalenyloxy)propane

To a 1 l. one-neck round bottom flask fitted with a nitrogen inlet tube and addition funnel was added 7.05 g (220 mmol) of 1-carboxy-1-phenyl-3-(4-methyl-1-naphthalenyloxy)propane and 400 ml of acetone. To the mixture was added 3.2 ml (22.9 mmol) of triethylamine and the resulting mixture was cooled to approximately 0° C. To the mixture was added 2.2 ml of ethyl chloroformate dropwise. The mixture was stirred 30 minutes at about 0° C. and 2.72 g (41.8 mmol) of sodium azide dissolved and a small amount of water was added dropwise. The mixture was stirred for about 60 minutes at about 0° C. and 200 ml of toluene was added. Water was added to the reaction mixture and the aqueous phase was separated and extracted twice with 200 ml of toluene. The organic extracts were combined, washed with water and a saturated sodium chloride solution, and dried over anhydrous sodium sulfate. The sodium sulfate was removed by filtration, and the filtrate was heated on a steam bath for two hours to induce formation of the isocyanate. The mixture was concentrated under vacuum to provide 7.6 g of the title compound which was used directly in the following reaction.

D. The 1-isocyanato-1-phenyl-3-(4-methyl-1-naphthalenyloxy)propane (6.98 g, 22.0 mmol) dissolved in 400 ml of dioxane was combined with 100 ml of a 8N hydrochloric acid. The mixture was stirred at room temperature for approximately three hours. The mixture was concentrated under vacuum and made basic with sodium hydroxide. The mixture was extracted with diethyl ether, and the organic extracts were washed twice with water, once with a saturated sodium chloride solution and dried over anhydrous sodium sulfate. The organic phase was concentrated under vacuum to provide 6.15 g of an oil. The oil was chromatographed over silica gel to provide 4.9 g of 1-phenyl-3-(4-methyl-1-naphthalenyloxy)propanamine. A small portion of the free base was combined with oxalic acid in a mutual solvent to provide 380 mg of the title compound. mp=191°–193° C.

Analysis calculated for $C_{22}H_{23}NO_5$: Theory: C, 69.28; H, 6.08; N, 3.67; Found: C, 69.56; H, 5.79; N, 3.86.

EXAMPLE 2

N,N-Dimethyl-1-phenyl-3-(4-methyl-1-naphthalenyloxy)propanamine oxalate

A 250 ml three-neck round bottom flask was charged with 2.2 g (7.6 mmol) of 1-phenyl-3-(4-methyl-1-naphthalenyloxy)propanamine and 100 ml of acetonitrile. To the mixture was added a 37% formaldehyde solution (3.02 ml, 37.8 mmol). The mixture was stirred for approximately 20 minutes while moderate heat was applied to maintain the reaction mixture as a solution. Next, 760 mg (12.1 mmol) of sodium cyanoborohydride was added to the reaction mixture, and the mixture was stirred for five hours at room temperature. The pH of the reaction mixture was maintained at approximately 6.5 by the addition of glacial acetic acid. The reaction mixture was acidified and stirred for 30 minutes. The mixture was concentrated under vacuum and made basic by the addition of 5N sodium hydroxide. Ten drops of triethylamine were added. The mixture was extracted three times with diethyl ether, and the organic extracts were combined and washed with water and a saturated sodium chloride solution, and dried over anhydrous sodium sulfate. The organic phase was concentrated under vacuum to provide 2.6 g of an oil. The oil was purified by high pressure liquid chromatography employing a methanol/methylene chloride gradient as the eluent. The free base was converted to the oxalate salt and recrystallized from ethyl acetate to provide 1.5 g of the title compound. mp=110°–112.5° C.

Analysis calculated for $C_{24}H_{27}NO_5$: Theory: C, 70.40; H, 6.65; N, 3.42; Found: C, 70.18; H, 6.42; N, 3.30.

EXAMPLE 3

N-Methyl-1-phenyl-3-(4-methyl-1-naphthalenyloxy)-propanamine oxalate

A. N-Ethoxycarbonyl-1-phenyl-3-(4-methyl-1-naphthalenyloxy)propanamine

A solution of 2.12 g (7.3 mmol) of 1-phenyl-3-(4-methyl-1-naphthalenyloxy)propanamine, 1.12 ml (8.0 mmol) of triethylamine and 100 ml of THF was cooled to approximately 0° C. under a nitrogen atmosphere. To the mixture was added 0.766 ml (8.0 mmol) of ethyl chloroformate dropwise. The resulting mixture was stirred at room temperature for approximately five and one-half hours and concentrated under vacuum. The residue was dissolved in diethyl ether, toluene and water. The mixture was extracted with diethyl ether. The organic extracts were combined, washed with water, 2N hydrochloric acid, water, 1N sodium hydroxide water, and a saturated sodium chloride solution and dried over anhydrous sodium sulfate. The mixture was concentrated under vacuum to provide 2.74 g of the title compound.

B. A 250 ml three-neck round bottom flask was charged with 3.6 g (94.5 mmol) of lithium aluminum hydride and 50 ml of THF. To the mixture was added a solution of 2.64 g (7.3 mmol) of N-ethoxycarbonyl-1-phenyl-3-(4-methyl-1-naphthalenyloxy)propanamine dissolved in 100 ml of THF dropwise. The mixture was heated to 40° C. and cooled to room temperature. The mixture was cooled to approximately 0° C. and a solution of sodium sulfate was added dropwise. The mixture was filtered and the mother liquor was concentrated under vacuum. The resulting residue was dissolved in diethyl ether. The organic solution was dried over anhydrous silica gel and concentrated under vacuum to provide 2.17 g of an oil. The oil was chromatographed over silica gel to provide 1.9 g of an oil. This oil was converted to the oxalate salt with oxalic acid and recrystallized from ethyl acetate/methanol to provide 1.74 g of the title compound. mp=173°–176° C.

Analysis calculated for $C_{23}H_{25}NO_5$: Theory: C, 69.86; H, 6.37; N, 3.54; Found: C, 69.67; H, 6.28; N, 3.41.

Following the general procedures outlined above, the following additional compounds as illustrated in Examples 4–24 were synthesized.

EXAMPLE 4

1-Phenyl-3-(4-methoxy-1-naphthalenyloxy)propanamine oxalate, mp=164°–166° C.

Analysis calculated for $C_{22}H_{23}NO_6$: Theory: C, 66.49; H, 5.83; N, 3.52; Found: C, 66.76; H, 6.05; N, 3.81.

EXAMPLE 5

N,N-Dimethyl-1-phenyl-3-(4-methoxy-1-naphthalenyloxy)propanamine oxalate, mp=148°–150° C.

Analysis calculated for $C_{24}H_{27}NO_6$: Theory: C, 67.75; H, 6.40; N, 3.29; Found: C, 67.55; H, 6.35; N, 3.26.

EXAMPLE 6

1-[2-(Trifluoromethyl)phenyl]-3-(1-naphthalenyloxy)propanamine oxalate, mp=184°–185° C.

Analysis calculated for $C_{22}H_{20}F_3NO_5$: Theory: C, 60.69; H, 4.63; N, 3.22; Found: C, 60.75; H, 4.60; N, 3.17.

EXAMPLE 7

N,N-Dimethyl-1-[2-(trifluoromethyl)phenyl]-3-(1-naphthalenyloxy)propanamine oxalate, mp=177°–179° C.

Analysis calculated for $C_{24}H_{24}F_3NO_5$: Theory: C, 62.20; H, 5.22; N, 3.02; Found: C, 62.42; H, 5.30; N, 3.25.

EXAMPLE 8

1-[3-(Trifluoromethyl)phenyl]-3-(1-naphthalenyloxy)propanamine oxalate, mp=177°–180° C.

Analysis calculated for $C_{22}H_{20}F_3NO_5$: Theory: C, 60.69; H, 4.63; N, 3.22; Found: C, 60.41; H, 4.46; N, 3.20.

EXAMPLE 9

N,N-Dimethyl-1-[3-(trifluoromethyl)phenyl]-3-(1-naphthalenyloxy)propanamine oxlate, mp=177°–179° C.

Analysis calculated for $C_{24}H_{24}F_3NO_5$: Theory: C, 62.20; H, 5.22; N, 3.02; Found: C, 62.43; H, 5.28; N, 2.99.

EXAMPLE 10

1-(2-Chlorophenyl)-3-(1-naphthalenyloxy)propanamine oxalate, mp=171°–173° C. dec.

Analysis calculated for $C_{21}H_{20}ClNO_5$: Theory: C, 62.77; H, 5.02; N, 3.49; Found: C, 62.70; H, 5.17; N, 3.70.

EXAMPLE 11

N,N-Dimethyl-1-(2-chlorophenyl)-3-(1-naphthalenyloxy)propanamine oxalate, mp=147°–148.5° C.

Analysis calculated for $C_{23}H_{24}ClNO_5$: Theory: C, 64.26; H, 5.63; N, 3.26; Found: C, 64.12; H, 5.39; N, 3.35.

EXAMPLE 12

1-(3-Chlorophenyl)-3-(1-naphthalenyloxy)propanamine oxalate, mp=178°–180° C.

Analysis calculated for $C_{21}H_{20}ClNO_5$: Theory: C, 62.77; H, 5.02; N, 3.49; Found: C, 62.51; H, 4.91; N, 3.47.

EXAMPLE 13

N,N-Dimethyl-1-(3-chlorophenyl)-3-(1-naphthalenyloxy)propanamine oxalate, mp=124°–126° C.

Analysis calculated for $C_{23}H_{24}ClNO_5$: Theory: C, 64.26; H, 5.63; N, 3.26; Found: C, 62.65; H, 5.56; N, 3.06.

EXAMPLE 14

1-(4-Chlorophenyl)-3-(1-naphthalenyloxy)propanamine oxalate, mp=192°–193.5° C. dec.

Analysis calculated for $C_{21}H_{20}ClNO_5$: Theory: C, 62.77; H, 5.02; N, 3.49; Found: C, 62.57; H, 5.03; N, 3.50.

EXAMPLE 15

N,N-Dimethyl-1-(4-chlorophenyl)-3-(1-naphthalenyloxy)propanamine oxalate, mp=141°–142.5° C.

Analysis calculated for $C_{23}H_{24}ClNO_5$: Theory: C, 64.26; H, 5.63; N, 3.26; Found: C, 64.06; H, 5.50; N, 3.22.

EXAMPLE 16

1-(4-Methoxyphenyl)-3-(1-naphthalenyloxy)propanamine oxalate, mp=181°–183° C.

Analysis calculated for $C_{22}H_{23}NO_6$: Theory: C, 66.49; H, 5.83; N, 3.52; Found: C, 66.31; H, 6.09; N, 3.57.

EXAMPLE 17

N,N-Dimethyl-1-(4-methoxyphenyl)-3-(1-naphthalenyloxy)propanamine oxalate, mp=123°–126° C.

Analysis calculated for $C_{24}H_{27}NO_6$: Theory: C, 67.75; H, 6.40; N, 3.29; Found: C, 67.50; H, 6.12; N, 3.34.

EXAMPLE 18

1-(3-Methoxyphenyl)-3-(1-naphthalenyloxy)propanamine hydrochloride, mp=164°–166° C.

Analysis calculated for $C_{20}H_{22}ClNO_2$: Theory: C, 69.86; H, 6.45; N, 4.07; Found: C, 70.07; H, 6.68; N, 4.02.

EXAMPLE 19

N,N-Dimethyl-1-(3-methoxyphenyl)-3-(1-naphthalenyloxy)propanamine oxalate, mp=115°–116.5° C.

Analysis calculated for $C_{24}H_{27}NO_6$: Theory: C, 67.75; H, 6.40; N, 3.29; Found: C, 67.58; H, 6.51; N, 3.25.

EXAMPLE 20

1-(2-Methoxyphenyl)-3-(1-naphthalenyloxy)propanamine oxalate, mp=177°–178.5° C.

Analysis calculated for $C_{22}H_{23}NO_6$: Theory: C, 66.49; H, 5.83; N, 3.52; Found: C, 66.66; H, 5.69; N, 3.47.

EXAMPLE 21

N,N-Dimethyl-1-(2-methoxyphenyl)-3-(1-naphthalenyloxy)propanamine oxalate, mp=109°–110° C.

Analysis calculated for $C_{24}H_{27}NO_6$: Theory: C, 67.75; H, 6.40; N, 3.29; Found: C, 64.24; H, 6.06; N, 3.03.

EXAMPLE 22

1-[3,4-(Methylenedioxy)phenyl]-3-(1-naphthalenyloxy)propanamine oxalate, mp=178°–179° C.

Analysis calculated for $C_{22}H_{21}NO_7$: Theory: C, 64.23; H, 5.15; N, 3.40; Found: C, 64.08; H, 5.11; N, 3.48.

EXAMPLE 23

N,N-Dimethyl-1-[3,4-(methylenedioxy)phenyl]-3-(1-naphthalenyloxy)propanamine oxalate, mp=144°-145° C.

Analysis calculated for $C_{24}H_{25}NO_7$: Theory: C, 65.59; H, 5.73; N, 3.19; Found: C, 65.59; H, 5.73; N, 3.06.

EXAMPLE 24

N-Methyl-1-phenyl-3-(1-naphthalenyloxy)propanamine oxalate, mp=131°-133° C.

Analysis calculated for $C_{23}H_{23}NO_7$: Theory: C, 64.93; H, 5.45; N, 3.29; Found: C, 64.68; H, 5.50; N, 3.32.

EXAMPLE 25

N,N-Dimethyl-1-(4-fluorophenyl)-3-(1-naphthalenyloxy)propanamine oxalate

A. 3-Amino-3-(4-fluorophenyl)propionic acid

A solution of 24.8 g (0.2 mol) of 4-fluorobenzaldehyde, 20.8 g (0.2 mol) of malonic acid, 30.8 g (0.4 mol) of ammonium acetate and 550 ml of ethanol was refluxed for approximately seven hours. The mixture was cooled and the precipitated solid was collected by vacuum filtration. The solid was recrystallized from 500 ml of water to provide 8.66 g of 3-amino-3-(4-fluorophenyl)propionic acid. mp=225° C. dec.

Analysis calculated for $C_9H_{10}FNO_2$: Theory: C, 59.01; H, 5.50; N, 7.65; Found: C, 58.83; H, 5.35; N, 7.58.

B. 3-Dimethylamino-3-(4-fluorophenyl)propionic acid

A mixture of 8.35 g (0.046 mol) of 3-amino-3-(4-fluorophenyl)propionic acid and formaldehyde in ethanol was reacted in the presence of hydrogen gas. The reaction mixture was concentrated under vacuum and the resulting residue was recrystallized from ethanol to provide 4.25 g of 3-dimethylamino-3-(4-fluorophenyl)propionic acid. mp=146°-148° C. dec.

Analysis calculated for $C_{11}H_{14}FNO_2$: Theory: C, 62.55; H, 6.68; N, 6.33; Found: C, 62.49; H, 6.75; N, 6.58.

C. Ethyl 3-dimethylamino-3-(4-fluorophenyl)propionate

A cold solution of 4.0 g of 3-dimethylamino-3-(4-fluorophenyl)propionic acid in 75 ml of ethanol was saturated with hydrogen chloride gas. The mixture was heated at reflux for approximately 16 hours and cooled to room temperature. The mixture was concentrated under vacuum and the residue was dissolved in water. The resulting mixture was washed with diethyl ether and the aqueous phase was made basic with 5N sodium hydroxide. The aqueous phase was extracted twice with diethyl ether and the ether extracts were combined, and washed with water, and a saturated sodium chloride solution, and dried over anhydrous sodium sulfate. The organic phase was concentrated under vacuum to provide 2.83 g of ethyl 3-dimethylamino-3-(4-fluorophenyl)propionate as an oil.

D. 3-Dimethylamino-3-(4-fluorophenyl)propanol

Ethyl 3-dimethylamino-3-(4-fluorophenyl)propionate (2.8 g) (0.011 mol) was dissolved in a suitable solvent and reduced in the presence of Red-Al (3.4M solution of sodium bis(2-methoxyethoxy)aluminum hydride in toluene from Aldrich Chemical Company, Milwaukee, Wis.). The reaction mixture was concentrated under vacuum to provide 2.19 g of 3-dimethylamino-3-(4-fluorophenyl)propanol as a solid.

E. A mixture of 0.44 g (0.11 mol) of 60% sodium hydride in mineral oil was slurried in 10 ml of dimethylacetamide under a nitrogen atmosphere. To this mixture was added 2.19 g (0.011 mol) of 3-dimethylamino-3-(4-fluorophenyl)propanol dissolved in 30 ml of dimethylacetamide. The mixture was heated for approximately 1 hour at 50° C. and 1.6 g (0.011 mol) of 1-fluoronaphthalene was added to the reaction mixture. The mixture was stirred at about 100° C. for 3 hours under a nitrogen atmosphere, cooled to room temperature and poured into approximately 100 ml of cold water. The mixture was extracted with diethyl ether. The ether extracts were combined and washed with water and a saturated sodium chloride solution. The organic phase was dried over anhydrous sodium sulfate and concentrated under vacuum to provide 3.24 g of an oil. The oil was purified employing high pressure liquid chromatography using methylene chloride as the eluent. Fractions containing the major component were combined and the solvent was evaporated therefrom to provide 2.16 g of an oil. This oil was converted to the oxalate salt and recrystallized from ethanol to provide the title compound. mp=133°-135° C.

Analysis calculated for $C_{23}H_{24}FNO_5$: Theory: C, 66.82; H, 5.85; N, 3.39; Found: C, 66.90; H, 6.17; N, 3.23.

The compounds of Examples 26–32 were synthesized following the general procedure described in Example 25.

EXAMPLE 26

N,N-Dimethyl-1-(4-methylphenyl)-3-(1-naphthalenyloxy)propanamine oxalate, mp=128°-130° C.

Analysis calculated for $C_{24}H_{27}NO_5$: Theory: C, 70.40; H, 6.65; N, 3.42; Found: C, 70.28; H, 6.39; N, 3.39.

EXAMPLE 27

N,N-Dimethyl-1-phenyl-3-(1-naphthalenyloxy)propanamine oxalate, mp=116°-118° C.

Analysis calculated for $C_{23}H_{25}NO_5$: Theory: C, 69.86; H, 6.37; N, 3.54; Found: C, 70.02; H, 6.37; N, 3.43.

EXAMPLE 28

N,N-Dimethyl-1-phenyl-3-(1-naphthalenyloxy)propanamine p-toluenesulfonate, mp=98°-100° C. dec.

Analysis calculated for $C_{28}H_{31}NO_4S$: Theory: C, 70.40; H, 6.54; N, 2.93; Found: C, 70.29; H, 6.55; N, 3.16.

EXAMPLE 29

N,N-Dimethyl-1-phenyl-3-[4-(trifluoromethyl)-1-naphthalenyloxy)propanamine oxalate, mp=93°-96° C.

Analysis calculated for $C_{24}H_{24}F_3NO_5$: Theory: C, 62.20; H, 5.22; N, 3.02; Found: C, 61.93; H, 5.49; N, 2.82.

EXAMPLE 30

N,N-Dimethyl-1-(2-methylphenyl)-3-(1-naphthalenyloxy)propanamine oxalate, mp=145°-148° C. dec.

Analysis calculated for $C_{24}H_{27}NO_5$: Theory: C, 70.40; H, 6.65; N, 3.42; Found: C, 70.50; H, 6.42; N, 3.38.

EXAMPLE 31

N,N-Dimethyl-1-[4-(trifluoromethyl)phenyl]-3-(1-naphthalenyloxy)propanamine oxalate, mp=155° C. dec.

Analysis calculated for $C_{24}H_{24}F_3NO_5$: Theory: C, 62.20; H, 5.22; N, 3.02; Found: C, 62.15; H, 5.28; N, 3.29.

EXAMPLE 32

N,N-Dimethyl-1-(3-methylphenyl)-3-(1-naphthalenyloxy)propanamine oxalate, mp=140° C. dec.

Analysis calculated for $C_{24}H_{27}NO_5$: Theory: C, 70.40; H, 6.65; N, 3.42; Found: C, 70.38; H, 6.57; N, 3.35.

EXAMPLE 33

N-Methyl-1-phenyl-3-(1-naphthalenyloxy)propanamine oxalate

A. 1-Phenyl-3-(1-naphthalenyloxy)propane

To a warm solution of 19.3 g (0.3 mol) of potassium hydroxide pellets dissolved in 300 ml of methanol was added 43.3 g (0.3 mol) of 1-naphthol. To the solution was added 39.8 g (0.2 mol) of 3-phenylpropylbromide. The mixture was refluxed for approximately 18 hours and concentrated under vacuum. To the mixture was added approximately 500 ml of diethyl ether and 300 ml of water. The layers were separated and the organic phase was washed with water, 5N sodium hydroxide, twice with water and a saturated sodium chloride solution. The organic phase was dried over anhydrous sodium sulfate and concentrated under vacuum to provide 49.24 g of an oil. The oil was purified by high pressure liquid chromatography employing hexanes/ethyl acetate as the eluent. Fractions containing the major component were combined and solvent was evaporated therefrom to provide 43.28 g of 1-phenyl-3-(1-naphthalenyloxy)propane as an oil.

Analysis calculated for $C_{19}H_{18}O$: Theory: C, 86.99; H, 6.92; Found: C, 86.74; H, 6.99.

B. 1-Bromo-1-phenyl-3-(1-naphthalenyloxy)propane

A mixture of 26.2 g (0.1 mol) of 1-phenyl-3-(1-naphthalenyloxy)propane, 17.8 g (0.1 mol) of N-bromosuccinimide, 120 ml of carbon tetrachloride and 250 mg of benzoyl peroxide was heated at 80° C. for four hours. The mixture was cooled and the precipitated solid was collected by vacuum filtration. The mother liquor was concentrated under vacuum to provide 34.26 g of a red oil.

C. A mixture of 18.8 g (0.055 mol) of 1-bromo-1-phenyl-3-(1-naphthalenyloxy)propane and 50 ml of monomethylamine dissolved in 200 ml of ethanol was reacted at 100° C. for 16 hours. The reaction mixture was cooled and concentrated under vacuum. The resulting residue was slurried in diethyl ether, water and 5N sodium hydroxide. The ether layer was separated and the aqueous phase was extracted twice with diethyl ether. The ether extracts were combined and washed with water. The ether extracts were next extracted twice with 2N hydrochloric acid and once with water. The aqueous extracts were combined, cooled and made basic with 5N sodium hydroxide. The aqueous phase was extracted three times with diethyl ether and the ether extracts were combined, washed with a saturated sodium chloride solution, and dried over anhydrous sodium sulfate. The sodium sulfate was removed by filtration and the filtrate was concentrated under vacuum to provide 7.15 g of an oil. The residue was solubilized in warm ethyl acetate and oxalic acid was added. The resulting oxalate salt was crystallized from ethanol to provide 6.06 g of the title compound.

While the product was present in the solid isolated above, a second compound, probably the 4-bromonaphthalenyloxy derivative, was also present. As such, 2.1 g of the solid was reacted with hydrogen in the presence of a 5% palladium-on-carbon in ethanol at room temperature. The mixture was filtered through celite and the filtrate was concentrated under vacuum. The resulting oil was dissolved in diethylether and water and 2N sodium hydroxide was added. The ether layer was separated and washed with a saturated sodium chloride solution and dried over anhydrous sodium sulfate. Following filtration to remove the sodium sulfate the filtrate was concentrated under vacuum to provide 1.71 g of an oil. The oil was converted to the oxalate salt in ethyl acetate. The resulting solid was recrystallized from ethanol and dried under vacuum at 100° C. to provide 1.73 g of the title compound. mp=206° C. dec.

Analysis calculated for $C_{22}H_{23}NO_5$: Theory: C, 69.28; H, 6.08; N, 3.67; Found: C, 69.46; H, 6.03; N, 3.71.

The compounds of Examples 34 and 35 were synthesized by the general procedure set forth in Example 33.

EXAMPLE 34

N,N-Dimethyl-1-phenyl-3-(4-chloro-1-naphthalenyloxy)propanamine oxalate, mp=144°–146° C. dec.

Analysis calculated for $C_{23}H_{24}ClNO_5$: Theory: C, 64.26; H, 5.63; N, 3.26; Found: C, 64.49; H, 5.89; N, 3.28.

EXAMPLE 35

1-Phenyl-3-(1-naphthalenyloxy)propanamine oxalate, mp=197°–198° C.

Analysis calculated for $C_{21}H_{21}NO_5$: Theory: C, 68.65; H, 5.76; N, 3.81; Found: C, 68.46; H, 5.69; N, 3.90.

EXAMPLE 36

(+)-N,N-Dimethyl-1-phenyl-3-(1-naphthalenyloxy)propanamine (+)-tartrate

N,N-dimethyl-1-phenyl-3-(1-naphthalenyloxy)propanamine (32.44 g, 0.106 mol) was dissolved in 75 ml of ethanol and combined with 15.94 g (0.106 mol) of (+)-tartaric acid dissolved in 650 ml of water. The mixture was allowed to stand at room temperature overnight and the precipitated solid was vacuum filtered. The title compound (2.55 g) was isolated in enantiomerically pure form following seven recrystallizations from acetone. mp=94°–96° C.

Analysis calculated for $C_{25}H_{29}NO_7$: Theory: C, 65.92; H, 6.42; N, 3.08; Found: C, 65.62; H, 6.48; N, 3.00.

EXAMPLE 37

(−)-N,N-Dimethyl-1-phenyl-3-(1-naphthalenyloxy)propanamine (−)-tartrate

The title compound was resolved from N,N-dimethyl-1-phenyl-3-(1-naphthalenyloxy)propanamine with (−)-tartaric acid following the general procedure set forth in Example 36. mp=119°–121° C. The product was determined to be enantiomerically pure after four recrystallizations from acetone.

Analysis calculated for $C_{25}H_{29}NO_7$: Theory: C, 65.92; H, 6.42; N, 3.08; Found: C, 64.89; H, 6.76; N, 3.05.

EXAMPLE 38

(+)-N,N-Dimethyl-1-phenyl-3-(1-naphthalenyloxy)propanamine (+)-3-bromocamphor-8-sulfonate To a solution of 15.3 g of N,N-dimethyl-1-phenyl-3-(1-naphthalenyloxy)propanamine in 400 ml of methanol were added 16.4 g of (+)-3-bromocamphor-8-sulfonic acid ammonium salt. The mixture was heated at reflux for 30 minutes, filtered, and concentrated in vacuo. Two hundred milliliters of ethyl acetate were added and, after standing overnight, the resulting colorless precipitate was collected by filtration. Sequential crystallizations from isopropanol and ethanol provided 3.89 g of the desired title product in enantiomerically pure form, m.p. 175–177° C.

Analysis for $C_{31}H_{38}BrNO_5S$: Theory: C, 60.39; H, 6.21; N, 2.27; Found: C, 60.63; H, 6.48; N, 2.31.

As noted above, the compounds of this invention are useful for selectively inhibiting the uptake of serotonin. Therefore, another embodiment of the present invention is a method for inhibiting serotonin uptake in mammals which comprises administering to a mammal requiring increased neurotransmission of serotonin a pharmaceutically effective amount of a compound of the invention.

The term "pharmaceutically effective amount", as used herein, represents an amount of a compound of the invention which is capable of inhibiting serotonin uptake. The particular dose of compound administered according to this invention will, of course, be determined by the particular circumstances surrounding the case, including the compound administered, the route of administration, the particular condition being treated, and similar considerations. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

The compounds can be administered by a variety of routes including the oral, rectal, transdermal, subcutaneous, intravenous, intramuscular or intranasal routes. It is a special feature of the compounds that they have a prolonged duration of action, and therefore are capable of inhibiting the uptake of serotonin for an extended period of time. It is also a special feature of the compounds of the present invention that they have been found to demonstrate a low degree of toxicity to mammals. Finally, it is a special feature of the compounds of the invention that they are extremely selective as inhibitors of serotonin reuptake relative to other monoamine reuptake.

A variety of physiologic functions have been shown to be subject to influence by brain serotoninergic neural systems. As such, the compounds of the present invention are believed to have the ability to treat a variety of disorders in mammals associated with these neural systems such as obesity, depression, alcoholism, pain, loss of memory, anxiety and smoking. Therefore, the present invention also provides methods of treating the above disorders at rates set forth above for inhibiting serotonin uptake in mammals.

The following experiment was conducted to demonstrate the ability of the compounds of the present invention to inhibit the uptake of serotonin. This general procedure is set forth by Wong et al., in *Drug Development Research* 6:397–403 (1985).

Male Sprague-Dawley rats (110–150 g) from Harlan Industries (Cumberland, Ind.) were fed Purina Chow ad libitum for at least 3 days before being used in the studies. Rats were killed by decapitation. Whole brains were removed and dissected. Cerebral cortex was homogenized in 9 volumes of a medium containing 0.32M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3$H-serotonin($^3$H-5-hydroxytryptamine, $^3$H-5HT) was determined as follows. Cortical synaptosomes (equivalent to 1 mg of protein) were incubated at 37° C. for 5 min in 1 ml of Krebs-bicarbonate medium containing also 10 mM glucose, 0.1 mM iproniazid, 1 mM ascorbic acid, 0.17 mM EDTA and 50 nM $^3$H-5HT The reaction mixture was immediately diluted with 2 ml of ice-chilled Krebs-bicarbonate buffer and filtered under vacuum with a cell harvester (Brandel, Gaithersburg, Md.). Filters were rinsed twice with approximately 5 ml of ice-chilled 0.9% saline and were transferred to a counting vial containing 10 ml of scintillation fluid (PCS, Amersham, Arlington Heights, Ill.). Radioactivity was measured by a liquid scintillation spectrophotometer. Accumulation of $^3$H-5HT at 4° C. represented the background and was subtracted from all samples.

The results of the evaluation of various compounds of the present invention are set forth below in Table I. In the Table, column 1 provides the Example Number of the compound evaluated; columns 2–5 identify the structure of the compounds evaluated when taken with the formula set forth in the heading; column 6 identifies the salt form of the compound evaluated; and column 7 provides the concentration of the test compound at $10^{-9}$M (nM) needed to inhibit 50% of serotonin (5HT), and is indicated in the Table as $IC_{50}$. The numbers in parentheses represent percent inhibition at 1000 nM.

TABLE I

INHIBITION OF 5HT UPTAKE IN VITRO

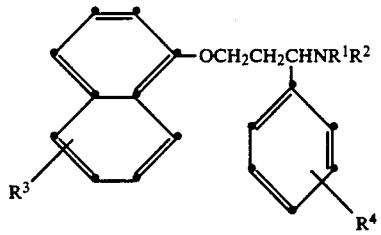

| Compound of Example No. | $R^1$ | $R^2$ | $R^3$ | $R^4$ | Salt Form | $IC_{50}$ (nM) 5HT |
|---|---|---|---|---|---|---|
| 1 | H | H | 4-CH$_3$ | H | oxalate | 90 |
| 2 | CH$_3$ | CH$_3$ | 4-CH$_3$ | H | oxalate | 25 |
| 3 | CH$_3$ | H | 4-CH$_3$ | H | oxalate | 37 |
| 4 | H | H | 4-OCH$_3$ | H | oxalate | (39%) |
| 5 | CH$_3$ | CH$_3$ | 4-OCH$_3$ | H | oxalate | 210 |
| 6 | H | H | H | 2-CF$_3$ | oxalate | 180 |
| 7 | CH$_3$ | CH$_3$ | H | 2-CF$_3$ | oxalate | 260 |
| 8 | H | H | H | 3-CF$_3$ | oxalate | (43%) |
| 9 | CH$_3$ | CH$_3$ | H | 3-CF$_3$ | oxalate | 500 |
| 10 | H | H | H | 2-Cl | oxalate | 76 |
| 11 | CH$_3$ | CH$_3$ | H | 2-Cl | oxalate | 33 |

TABLE I-continued
INHIBITION OF 5HT UPTAKE IN VITRO

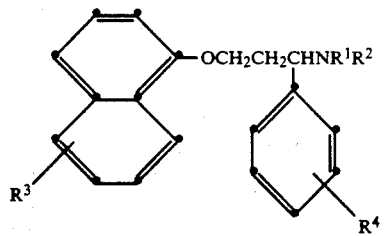

| Compound of Example No. | R¹ | R² | R³ | R⁴ | Salt Form | IC$_{50}$ (nM) 5HT |
|---|---|---|---|---|---|---|
| 12 | H | H | H | 3-Cl | oxalate | 150 |
| 13 | CH$_3$ | CH$_3$ | H | 3-Cl | oxalate | 72 |
| 14 | H | H | H | 4-Cl | oxalate | 400 |
| 15 | CH$_3$ | CH$_3$ | H | 4-Cl | oxalate | 110 |
| 16 | H | H | H | 4-OCH$_3$ | oxalate | 100 |
| 17 | CH$_3$ | CH$_3$ | H | 4-OCH$_3$ | oxalate | 32 |
| 18 | H | H | H | 3-OCH$_3$ | hydrochloride | 84 |
| 19 | CH$_3$ | CH$_3$ | H | 3-OCH$_3$ | oxalate | 29 |
| 20 | H | H | H | 2-OCH$_3$ | oxalate | (25%) |
| 21 | CH$_3$ | CH$_3$ | H | 2-OCH$_3$ | oxalate | 16 |
| 22 | H | H | H | 3,4-methylenedioxy | oxalate | 130 |
| 23 | CH$_3$ | CH$_3$ | H | 3,4-methylenedioxy | oxalate | 29 |
| 24 | CH$_3$ | H | H | 3,4-methylenedioxy | oxalate | 47 |
| 25 | CH$_3$ | CH$_3$ | H | 4-F | oxalate | 50 |
| 26 | CH$_3$ | CH$_3$ | H | 4-CH$_3$ | oxalate | 80 |
| 27 | CH$_3$ | CH$_3$ | H | H | oxalate | 10 |
| 29 | CH$_3$ | CH$_3$ | 4-CF$_3$ | H | oxalate | 800 |
| 30 | CH$_3$ | CH$_3$ | H | 2-CH$_3$ | oxalate | 10 |
| 31 | CH$_3$ | CH$_3$ | H | 4-CF$_3$ | oxalate | 195 |
| 32 | CH$_3$ | CH$_3$ | H | 3-CH$_3$ | oxalate | 13 |
| 33 | CH$_3$ | H | H | H | oxalate | 35 |
| 34 | CH$_3$ | CH$_3$ | 4-Cl | H | oxalate | 88 |
| 35 | H | H | H | H | oxalate | 80 |
| 36 | CH$_3$ (+ isomer) | CH$_3$ | H | H | tartrate | 10 |
| 37 | CH$_3$ (− isomer) | CH$_3$ | H | H | tartrate | 35 |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium) ointments containing, for example, up to 10% by weight of the active compound, soft and hard gelatin capsules, suppositories, sterile injectable solutions and sterile packaged powders.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

| | Quantity (mg/capsule) |
|---|---|
| (+)-N,N-dimethyl-1-phenyl-3-(1-naphthalenyloxy)propanamine tartrate | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

| | Quantiy (mg/tablet) |
|---|---|
| N,N-dimethyl-1-(3-methylphenyl)-3-(1-naphthalenyloxy)propanamine oxalate | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

| | Weight % |
|---|---|
| N-methyl-1-(4-fluorophenyl)-3-(1-naphthalenyloxy)propanamine hydrochloride | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

FORMULATION 4

Tablets each containing 60 mg of active ingredient are made as follows:

| (−)-N,N-dimethyl-1-phenyl-3-(1-naphthalenyloxy)propanamine tartrate | 60 mg |
|---|---|
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

| N,N-dimethyl-1-phenyl-3-(2-naphthalenyloxy)propanamine citrate | 80 mg |
|---|---|
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of active ingredient may be made as follows:

| 1-(3-chlorophenyl)-3-(1-naphthalenyloxy)propanamine oxalate | 225 mg |
|---|---|
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| N,N-dimethyl-1-phenyl-3-(1-naphthalenyloxy)propanamine oxalate | 50 mg |
|---|---|
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

We claim:

1. A compound of the formula

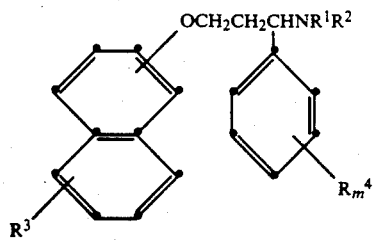

wherein:
  each of $R^1$ and $R^2$ independently is hydrogen or methyl;
  $R^3$ is hydrogen, halo, $C_1$-$C_4$ alkyl, $C_1$-$C_3$ alkoxy or trifluoromethyl;
  each $R^4$ independently is hydrogen, halo, $C_1$-$C_4$ alkyl, $C_1$-$C_3$ alkoxy or trifluoromethyl;
  m is 1 or 2;
  when m is 2, each $R^4$ can be combined to form methylenedioxy; or a pharmaceutically acceptable acid addition salt thereof.

2. A compound of claim 1 wherein both $R^1$ and $R^2$ are hydrogen.

3. A compound of claim 1 wherein one of $R^1$ and $R^2$ is hydrogen and the other is methyl.

4. The compound of claim 1 wherein both of $R^1$ and $R^2$ are methyl.

5. The compound of claim 4 which is N,N-dimethyl-1-phenyl-3-(1-naphthalenyloxy)propanamine, or a pharmaceutically acceptable acid addition salt thereof.

6. A compound of claim 4 which is the (+) stereoisomer.

7. The compound of claim 6 which is (+)-N,N-dimethyl-1-phenyl-3-(1-naphthalenyloxy)propanamine, or a pharmaceutically acceptable acid addition salt thereof.

8. The compound of claim 7 which is (+)-N,N-dimethyl-1-phenyl-3-(1-naphthalenyloxy)propanamine tartrate.

9. The compound of claim 4 which is the (−)stereoisomer.

10. The compound of claim 9 which is (−)-N,N-dimethyl-1-phenyl-3-(1-naphthalenyloxy)propanamine, or a pharmaceutically acceptable acid addition salt thereof.

11. A compound of claim 10 which is (−)-N,N-dimethyl-1-phenyl-3-(1-naphthalenyloxy)propanamine tartrate.

12. A method for inhibiting serotonin uptake in mammals which comprises administering to a mammal requiring increased neurotransmission of serotonin a pharmaceutically effective amount of a compound of claim 1 or a pharmaceutically acceptable acid addition salt thereof.

13. A method of claim 12 wherein both $R^1$ and $R^2$ are methyl.

14. The method of claim 13 wherein the compound is N,N-dimethyl-1-phenyl-3-(1-naphthalenyloxy)propanamine, or a pharmaceutically acceptable acid addition salt thereof.

15. The method of claim 14 wherein the compound is N,N-dimethyl-1-phenyl-3-(1-naphthalenyloxy)propanamine tartrate.

16. The method of claim 15 wherein the (+)-stereoisomer of the compound is employed.

17. A method of claim 15 wherein the (−)-stereoisomer of the compound is employed.

18. A method of treating depression in humans comprising administering to a human suffering from depression an effective antidepressant dose of a compound of claim 1 or a pharmaceutically acceptable acid addition salt thereof.

19. A method of claim 18 wherein both $R^1$ and $R^2$ are methyl.

20. The method of claim 19 wherein the compound is N,N-dimethyl-1-phenyl-3-(1-naphthalenyloxy)propanamine, or a pharmaceutically acceptable acid addition salt thereof.

21. The method of claim 20 wherein the compound is N,N-dimethyl-1-phenyl-3-(1-naphthalenyloxy)propanamine tartrate.

22. The method of claim 21 wherein the (+)-stereoisomer of the compound is employed.

23. The method of claim 21 wherein the (−)-stereoisomer is employed.

24. A method of treating anxiety in humans comprising administering to a human suffering from anxiety an effective antianxiety dose of a compound of claim 1 or a pharmaceutically acceptable acid addition salt thereof.

25. A method of claim 24 wherein both $R^1$ and $R^2$ are methyl.

26. The method of claim 25 wherein the compound is N,N-dimethyl-1-phenyl-3-(1-naphthalenyloxy)propanamine, or a pharmaceutically acceptable acid addition salt thereof.

27. The method of claim 26 wherein the compound is N,N-dimethyl-1-phenyl-3-(1-naphthalenyloxy)propanamine tartrate.

28. The method of claim 27 wherein the (+)-stereoisomer of the compound is employed.

29. The method of claim 27 wherein the (−)-stereoisomer is employed.

30. A method of treating obesity in humans comprising administering to a human suffering from obesity an effective antiobesity dose of a compound of claim 1 or a pharmaceutically acceptable acid addition salt thereof.

31. A method of claim 30 wherein both $R^1$ and $R^2$ are methyl.

32. The method of claim 31 wherein the compound is N,N-dimethyl-1-phenyl-3-(1-naphthalenyloxy)propanamine, or a pharmaceutically acceptable acid addition salt thereof.

33. The method of claim 31 wherein the compound is N,N-dimethyl-1-phenyl-3-(1-naphthalenyloxy)propanamine tartrate.

34. The method of claim 33 wherein the (+)-stereoisomer of the compound is employed.

35. The method of claim 33 wherein the (−)-stereoisomer is employed.

36. A method of suppressing the desire of humans to smoke comprising administering to a human in need of such suppression an effective dose to relieve the desire to smoke of a compound of claim 1 or a pharmaceutically acceptable acid addition salt thereof.

37. A method of claim 36 wherein both $R^1$ and $R^2$ are methyl.

38. The method of claim 37 wherein the compound is N,N-dimethyl-1-phenyl-3-(1-naphthalenyloxy)propanamine, or a pharmaceutically acceptable acid addition salt thereof.

39. The method of claim 38 wherein the compound is N,N-dimethyl-1-phenyl-3-(1-naphthalenyloxy)-propanamine tartrate.

40. The method of claim 39 wherein the (+)-stereoisomer of the compound is employed.

41. The method of claim 39 wherein the (−)-stereoisomer is employed.

42. A method of suppressing the desire of humans to consume alcohol comprising administering to a human in need of such suppression an effective dose to relieve the desire to consume alcohol of a compound of claim 1 or a pharmaceutically acceptable acid addition salt thereof.

43. A method of claim 42 wherein both $R^1$ and $R^2$ are methyl.

44. The method of claim 43 wherein the compound is N,N-dimethyl-1-phenyl-3-(1-naphthalenyloxy)-propanamine, or a pharmaceutically acceptable acid addition salt thereof.

45. The method of claim 44 wherein the compound is N,N-dimethyl-1-phenyl-3-(1-naphthalenyloxy)-propanamine tartrate.

46. The method of claim 45 wherein the (+)-stereoisomer of the compound is employed.

47. The method of claim 45 wherein the (−)-stereoisomer is employed.

48. A pharmaceutical formulation comprising a compound of claim 1, or a pharmaceutically acceptable acid addition salt thereof and a pharmaceutically acceptable carrier, diluent or excipient therefor.

49. A formulation of claim 48 wherein both $R^1$ and $R^2$ are methyl.

50. The formulation of claim 49 wherein the compound is N,N-dimethyl-1-phenyl-3-(1-naphthalenyloxy)-propanamine, or a pharmaceutically acceptable acid addition salt thereof.

51. The formulation of claim 50 wherein the compound is N,N-dimethyl-1-phenyl-3-(1-naphthalenyloxy)-propanamine tartrate.

52. The formulation of claim 51 wherein the (+)stereoisomer of the compound is employed.

53. The formulation of claim 52 wherein the (−)-stereoisomer of the compound is employed.

* * * * *